United States Patent [19]

Koda et al.

[11] Patent Number: 4,938,928
[45] Date of Patent: Jul. 3, 1990

[54] GAS SENSOR

[75] Inventors: Hiroshi Koda; Muneharu Shimabukuro; Kiyonori Ono, all of Osaka, Japan

[73] Assignee: Figaro Engineering Inc., Osaka, Japan

[21] Appl. No.: 303,067

[22] Filed: Jan. 30, 1989

Related U.S. Application Data

[63] Continuation of Ser. No. 111,251, Oct. 22, 1987, abandoned.

[30] Foreign Application Priority Data

Oct. 28, 1986 [JP] Japan ................... 61-256082
Jan. 27, 1987 [JP] Japan ................... 62-16844

[51] Int. Cl.$^5$ .......................................... G01N 27/00
[52] U.S. Cl. .................................... 422/98; 338/34; 338/35; 422/90; 422/94; 422/95; 422/97
[58] Field of Search ............... 422/90, 94, 95, 97, 422/98; 338/34–35

[56] References Cited

U.S. PATENT DOCUMENTS

| | | | |
|---|---|---|---|
| 3,564,474 | 6/1968 | Firth et al. | 422/95 |
| 3,959,764 | 5/1976 | Allman | 422/90 |
| 4,007,435 | 2/1977 | Tien | 338/34 |
| 4,123,225 | 10/1978 | Jones et al. | 422/98 |
| 4,338,281 | 7/1982 | Treitinger et al. | 422/98 |
| 4,343,768 | 8/1982 | Kimura . | |
| 4,350,660 | 9/1982 | Robinson et al. | 422/98 |
| 4,407,778 | 10/1983 | Shirabori et al. | 422/98 |
| 4,423,407 | 12/1983 | Zucherman | 422/98 |
| 4,510,036 | 4/1985 | Takeuchi et al. | 338/34 |
| 4,688,014 | 8/1987 | Kitaguchi | 338/34 |
| 4,706,493 | 11/1987 | Chang et al. | 422/98 |

Primary Examiner—Robert J. Warden
Assistant Examiner—Lyle Alfandary Alexander
Attorney, Agent, or Firm—Armstrong, Nikaido, Marmelstein, Kubovcik & Murray

[57] ABSTRACT

A sensor comprising a metal heat generating member formed with a heat-resistant insulating coating of $Al_2O_3$ or the like over its surface, and an atmosphere-sensitive layer of $SnO_2$ or the like supported on the coating. The insulating coating is formed, for example, by alumina sol coating and thermal decomposition, or plasma CVD of an aluminum compound. The sensitive layer is formed, for example, by the thermal decomposition of an organic compound of tin, vacuum evaporation or sputtering of tin, or printing of $SnO_2$ on the heat generating member when the member is in the form of a flat plate. At least one electrode is connected to the sensitive layer for deriving an output from the layer in response to a combustible gas, humidity or the like.

6 Claims, 15 Drawing Sheets

Fig. 4 (a)
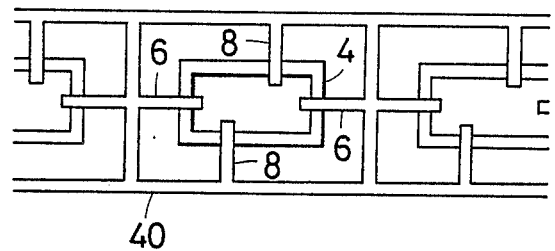
(b)
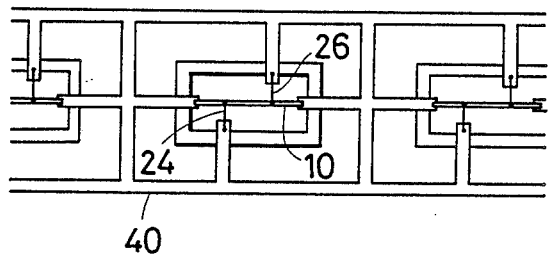
(c)
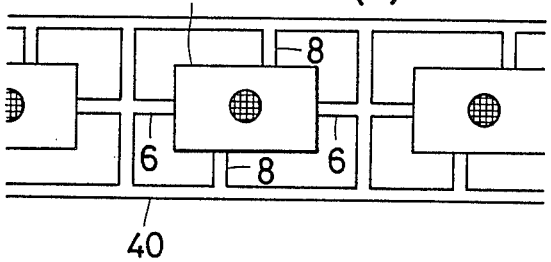
(d)
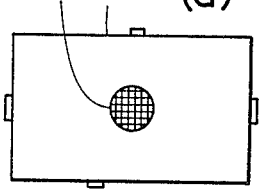

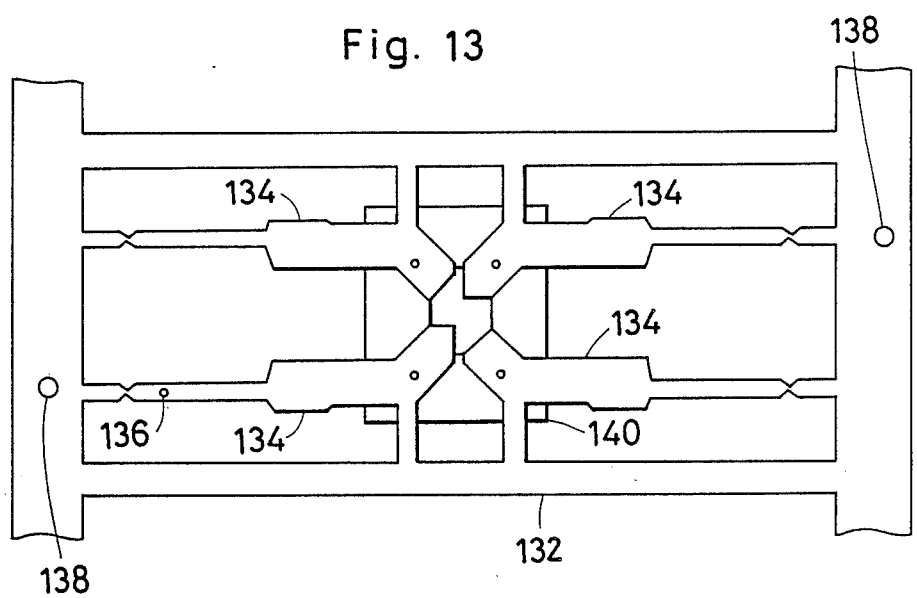
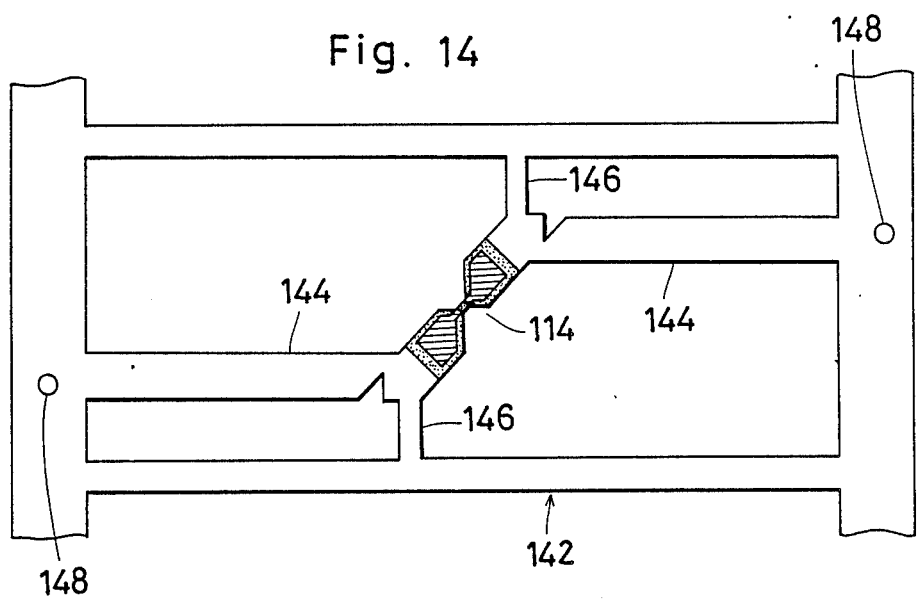

GAS SENSOR

This application is a continuation of applications Ser. No. 111,251 filed Oct. 22, 1987, now abandoned.

FIELD OF THE INVENTION

The present invention relates to a sensor for detecting components of atmospheres such as combustible gases, toxic gases, oxygen and water vapor, and a method of producing the same. More particularly, the invention relates to a sensor supported by a metal heat generating member serving as a heater and a method of producing the same. The invention further relates, for example, to the detection of oxygen, combustible gases, water vapor or the like utilizing variations in the resistance value of a metal oxide semiconductor, and to the detection of hydrogen, carbon monoxide, water vapor or the like using a proton conductor.

PRIOR ART

One of the basic problems in the field of gas sensors and humidity sensors is a reduction in power consumption. In this respect, U.S. Pat. No. 4,343,768 proposes to subject a silicon substrate formed with an $SiO_2$ coating to undercut etching at its lower portion and to provide a bridge of $SiO_2$ coating at the etched portion. The bridge is thin and slender and is diminished in heat capacity and thermal conductivity. A metal oxide semiconductor, such as $SnO_2$, and a heater are provided on the bridge to afford a gas sensor.

SUMMARY OF THE INVENTION

An object of the present invention is to reduce the power consumption of sensors by a solution different from the above and to provide a method of producing such sensors. Another object of the invention is to produce such sensors with greater ease and to further reduce the power consumption of sensors.

According to the invention, a metal heat generating member having a heat-resistant insulating coating on its surface serves as a support for a sensor.

More specifically, a noble metal such as Pt or Pd-Ir alloy or a base metal such as Fe-Cr-Al alloy or Ni-Cr alloy is formed with a heat-resistant insulating coating over the surface to provide a metal heat generating member for use in this invention. The coating can be formed, for example, by plasma CVD, sputtering, ion plating, vacuum evaporation or CVD. When suitable coating conditions are selected, a compact coating can be obtained easily as firmly bonded to the metal. Subsequently, an atmosphere-sensitive layer is provided on the coating, whereby a sensor can be obtained.

The atmosphere-sensitive layer is prepared from a substance whose resistance value or electromotive force varies on contact with the gas or water vapor to be detected. For example, the layer may be formed by a metal oxide semiconductor such as $SnO_2$, $In_2O_3$, $TiO_2$, $LaCoO_3$ or $BaSnO_3$ to detect a variation in its resistance value due to contact with a combustible gas, toxic gas, oxygen, water vapor or the like. Alternatively, a proton conductor may be used for the sensitive layer to detect a variation in its electromotive force due to hydrogen or carbon monoxide, or a variation in its resistance due to water vapor. At least one electrode is connected to the atmosphere-sensitive layer for detecting variations in resistance value or electromotive force.

The atmosphere-sensitive substance can be separated from the metal heat generating member by the insulating coating Many atmosphere-sensitive substances are metal oxides and are low in the strength of bond to metals. However, the insulating layer is usually formed of ceramics, almost completely eliminating the likelihood of the sensitive substance from dislodging or separating from the coating. Further if a heat generating member of base metal is brought into direct contact with the atmosphere-sensitive substance, there arises the problem of poisoning or deterioration of the sensitive substance by the base metal. However, the heat-resistant insulating substance coating the surface of the base metal member obviates this problem.

The configuration of the sensor is dependent on the metal heat generating member itself and can be made extremely small. Consequently, the member can be such as is sufficient to support itself against gravity, making the sensor compacter and resulting in a reduced heat capacity.

Generally, such sensors are fabricated by:
(1) forming a heat-resistant insulating coating at least partially on a metal heat generating member,
(2) providing an atmosphere-sensitive layer over the surface of the metal heat generating member so as to be supported at least partially on the coating, and
(3) connecting at least one electrode to the atmosphere-sensitive layer. The electrode may be provided before or after the layer is formed.

In the case where the heat generating member is made of base metal, it is desirable to separate the sensitive layer from the member by the insulating coating and to connect at least two electrodes to the sensitive layer. When the heat generating member is made of noble metal, the member may serve also as one of the two electrodes for the sensitive layer. In this case, the sensor can be such that a major portion of the sensitive layer is supported on the heat generating member, with only a minor portion of the layer supported on the insulating coating.

The electrode connected to the sensitive layer is connected to an external electrode, as a rule, by a lead wire. However, since it is difficult to attach the lead wire to the heat generating member which is small, the electrode may be connected directly to the external electrode. The lead connecting work can then be dispensed with. When the heat generating member itself is made small-sized and lower in thermal conductivity, noticeably increased power consumption will not result.

To assure diminished power consumption, it is desirable to make the metal heat generating member smaller. This however renders the member difficult to handle. It is therefore preferable to prepare a frame having a multiplicity of heat generating members attached thereto as arranged in series, form an insulating coating and atmosphere-sensitive layer on the frame, position the frame properly for external leads, and thereafter connect each member to the desired leads and separate the member from the frame. The generating member can then be positioned properly for the external leads and connected thereto with ease

BRIEF DESCRIPTION OF THE DRAWINGS

FIGS. 4 (a) to (d) are front views showing a procedure for assembling the sensor of FIG. 1;

FIG. 13 is a plan view showing external leads as arranged for a fifth embodiment;

FIG. 14 is a plan view showing a lead frame having connected thereto the metal heat generating member of the fifth embodiment;

DESCRIPTION OF THE PREFERRED EMBODIMENTS

First Embodiment

Construction of Sensor

Figure 1:
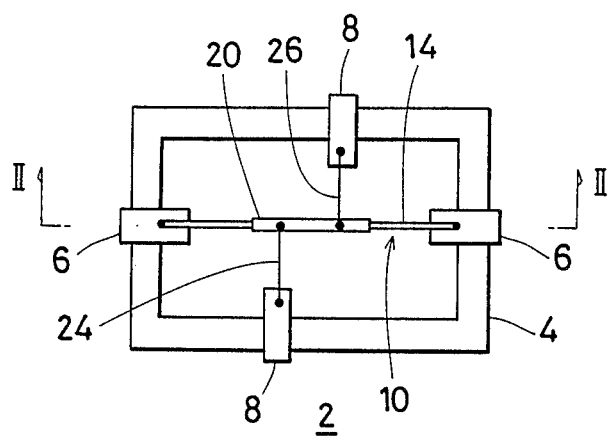
FIG. 1 is a front view showing a sensor as a first embodiment.

FIGS. 1 to 4 show a basic embodiment. With reference to FIG. 1, indicated at 2 is a sensor, and at 4 a housing of synthetic resin or the like. The assembly is covered with an unillustrated explosion-proof protective cover. Secured to the housing 4 are heater stems 6 and electrode stems 8. A sensor main body 10 comprises a metal heat generating member 14 having a heat-resistant insulating coating 18 thereon, and an atmosphere-sensitive layer 20 supported on the coating. Lead wires 24, 26 are connected to the sensitive layer 20 by a pair of electrodes 28, 28. The sensor main body 10 is accommodated in the hollow portion of the housing 4.

Figure 2:
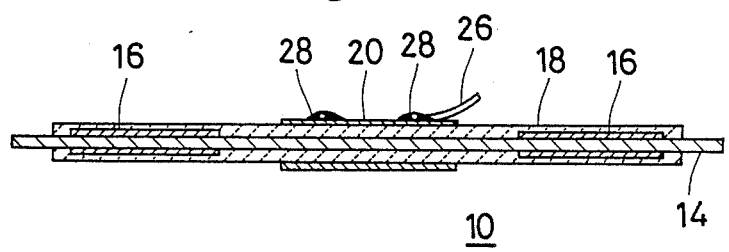
FIG. 2 is a fragmentary view in section taken along the line II—II in FIG. 1.
Figure 3:
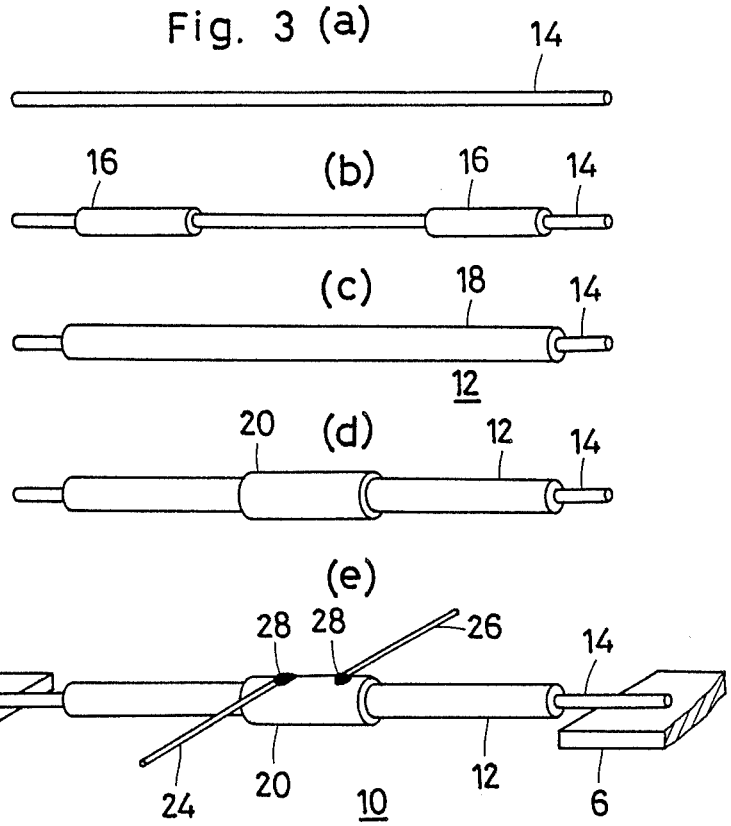
FIGS. 3 (a) to (e) are perspective views showing a method of producing the sensor of FIG. 1.

With reference to FIGS. 2 and 3, the heat generating member 14 is made of a noble metal material such as Pt, Ir, Pd 80-Ir 20 or Pt-ZGS (wherein $ZrO_2$ particles are separated out at Pt grain boundary), or a base metal material such as W, Fe-Cr-Al or Ni-Cr. Preferably, the member 14 is made of a material which is high in durability against atmospheric exposure, heat resistance and electric resistance. Especially preferable is a high-resistance base metal heat generating material. In this embodiment, an Fe-Cr-Al alloy wire was used (Kanthal wire, product of Kanthal, Sweden; Kanthal is a trademark of the company). The member is in the form of a wire having such a diameter as to support the sensitive layer 20 thereon and to permit connection of the lead wires 24, 26 to the layer. More specifically, it is sufficient that the wire diameter be about 10 micrometers, but in view of the difficulty to be encountered in wire drawing, the diameter is preferably about 20 to about 80 micrometers.

When required, the member 14 is formed with a coating 16 of gold or like good conductor in order to permit the member 14 to evolve heat concentrically under the sensitive layer 20 and reduce the power consumption. Thus, the conductor coating 16 is provided over the member 14 except where the electrodes 28, 28 are present to inhibit heat generation at the unnecessary portion. Of course, the conductor coating 16 need not always be formed.

The heat-resistant insulating coating 18 is formed over the surface of the heat generating member 14 except where the member is joined to the stems 6 as by welding. The coating 18 is made of a material which is stable to the atmosphere to which the sensor is exposed and nonreactive with the member 14 or with the sensitive layer 20, and exhibits high strength to bond to the member 14 and affords high insulation resistance between the member 14 and the layer 20. Examples of useful materials for the coating are metal oxides such as alumina and silica, ceramics such as SiC, $Si_3N_4$ and BN, high-melting-point glasses such as borosilicate glass, etc. Of these, alumina, silica and like metal oxides are desirable. The term "insulating" as used herein means that the coating 18 has sufficiently great insulation resistance relative to the internal resistance of the sensitive layer 20. For example, when the sensitive layer is made of $SnO_2$ of low resistance, $TiO_2$ of high resistance may be used for the coating 18. The coating 18 further acts to shield the member 14 from the atmosphere for protection.

The thickness of the coating 18, which is dependent on the bond strength and insulating properties, is preferably 50 angstroms to 10 micrometers, more preferably 100 angstroms to 5 micrometers.

The atmosphere-sensitive layer 20 is made of a material which is determined according to the component of atmosphere to be detected For example, metal oxide semiconductors such as $SnO_2$, $In_2O_3$ and $Fe_2O_3$ are used for detecting combustible gases and toxic gases. Metal oxide semiconductors such as $BaSnO_3$, $LaNiO_3$ and NiO are useful for detecting $O_2$. Ceramics such as $MgCr_2O_4$ and $TiO_2$ are useful for detecting the humidity of atmospheres. These materials physically adsorb water vapor and detect humidity from the electric conductivity of the adsorbed water. While the sensitive layer 20 is usable at room temperature when detecting humidities, the layer 20 is heat-cleaned using the member 14 to remove dust and oils from the layer 20. Examples of other materials that are usable are proton conductors such as antimonic acid ($H_2Sb_2O_6$) and antimony phosphate ($HSbP_2O_8$) These proton conductors produce an electromotive force due to a difference in the concentration of $H_2$ or carbon monoxide and are usable for detecting $H_2$ and carbon monoxide In this case, it is desirable, for example, to shield one of the electrodes from the atmosphere in order to create a difference in the concentration of hydrogen or the like between the two electrodes and produce an electromotive force.

Thus, materials are useful for the layer 20 provided that they undergo variations in electrical characteristics due to a gas component of the ambient atmosphere. The thickness of the sensitive layer 20 is such that the heat generating member 14 is capable of supporting the layer 20. For example when the layer 20 is formed by vacuum evaporation or sputtering, the thickness is preferably 100 angstroms to 5 micrometers. When the layer is formed by powder coating, dipping or printing, the thickness is preferably 1 micrometer to 50 micrometers. Any known material or method is usable as desired for forming the sensitive layer 20.

A gold wire, about 20 micrometers in diameter, is used as the lead wires 24, 26. These lead wires 24, 26 are connected to the sensitive layer 20 by fritless gold paste electrodes 28 and fixedly joined to the stems 8 by welding. The electrodes 28 may be provided on the insulating coating 18 before forming the layer 20. Production of Sensor A process of producing the sensor 2 will be described with reference to FIGS. 3 and 4. A metal heat generating member 14 in the form of a wire is prepared (FIG. 3 (a)). A conductor coating 16 of gold is formed on the member 15 at a specified spacing by paste printing or vacuum evaporation (FIG. 3 (b)). Subsequently, after the portions of the member 14 to be welded to the stems 6 are masked, a heat-resistant insulating coating 18 is formed (FIG. 3 (c)). When suitable welding conditions are selected, the member 14 as formed with the coating 18 can welded to the stems. The insulating coating 18 may be formed over the entire surface of the member 14. Most preferably, the coating 18 is formed by plasma CVD, sputtering or ion plating. In the case of plasma CVD, an organic compound such as an aluminum alkoxide is injected into a plasma of Ar or the like, and the mixture is applied to the member 14 to complete the coating 18. In the case of sputtering, the coating is formed, for example, by applying aluminum by reactive sputtering in a low oxygen pressure. Ion plating can be practiced similarly The insulating coating 18 can also be formed, for example, by the oxidation of a vacuum-deposited film of aluminum, alumina sol coating followed by sintering, or thermal decomposition of an organic compound such as aluminum isopropoxide Al-$(O-CH-(CH_3)_2)_3$.

These methods, i.e. plasma CVO, coating with alumina sol and sintering, and thermal decompostion of Al isopropoxide were checked for the bond strength and insulation strength of the resulting coating 18 When plasma CVD is resorted to, an alumina coating, even if 50 angstroms in thickness, gave insulation resistance of at least 1 megaohms between the electrode 28 and the heat generating member 14. In the case of sol coating or thermal decomposition of the isopropoxide, the coating, when obtained in the form of a single coat, had many pinholes. The application and sintering of sol, when repeated three to five times, gave a coating free from pinholes and having insulation resistance of at least 1 megaohms In the case of the thermal decomposition of Al isopropoxide, the member 14 was dipped in an isopropoxide solution and then subjected to thermal decomposition to obtain an alumina coating. In this case, about 7 to about 10 repeated dipping-decomposition cycles afforded a pinhole-free coating having insulation resistance of at least 1 megaohms.

In the case where the sensor wherein the insulating coating 18 is made of a metal oxide such as alumina or silica is to be used in a neutral non-oxidizing atmosphere, SiC, $Si_3N_4$, BN, TiC or the like is also usable as a material for the coating 18. Although the above examples are given with respect to alumina, coatings 18 of other corresponding materials can be obtained using silica sol in place of alumina sol or tetraethyl silicate in place of Al isopropoxide When plasma CVD was resorted to, the resulting alumina coating, even if 50 angstroms in thickness, exhibited sufficient bond strength and insulation resistance. Accordingly, the thickness of the coating 18 should preferably be at least 50 angstroms, more preferably at least 100 angstroms. The upper limit of the thickness of the coating 18, although not particularly significant, is preferably up to 10 micrometers, more preferably up to 5 micrometers.

The member 14 is masked, for example, by applying nylon or like resin to the portion thereof where the coating 18 need not be formed. For the same purpose, the coating formed can alternatively be etched away from the portion. For example when the alumina coating is to be etched away, a photoresist is applied to the coating, followed by exposure to light, removal of the resist and etching. Preferred etchants for alumina are HF (etching at room temperature) and warm phosphoric acid. It is also desirable to use HF at room temperature for silica.

The atmosphere-sensitive layer 20 is formed by vacuum evaporation, sputtering, powder coating or printing, or by dipping the member 14 in a dispersion of particles (FIG. 3 (d)). The layer 20 may alternatively be formed by the thermal decomposition of an organic compound such as tin octylate.

After the sensitive layer 20 has been formed, the electrodes 28 are attached to the layer, and the lead wires 24, 26 to the electrodes. The electrodes 28 may be attached to the coating 18 before forming the layer 20.

With reference to FIGS. 4 (a) to (d), the sensor main body is accommodated in the housing 4 in the following manner. A multiplicity of stems 6 and 8 are connected into an assembly of lead frames 40. The housing 4 is secured to each lead frame 40 as by fusion (FIG. 4 (a)). The heat generating member 14 provided with the sensitive layer 20 is fixedly joined to the frame 40 as by welding, and the electrodes 28 and the lead wires 24, 26 are attached to the member 14 (FIG. 4 (b)). For example, a gold paste is used for the electrodes 28 and is solidified at about 600° to about 800° C. The lead wires 24, 26 are then welded to the steps 8. The member 14 may be welded to the stems 6 first, and the layer 20 thereafter formed Further after attaching the electrodes 28 and lead wires 24, 26 to the member 14, the member 14 may be welded to the stems 8. After the above procedure, an upper cover 32 having an air vent 34 is attached to the housing 4 by fusion (FIG. 4 (c)). Subsequently, the unnecessary portions of the lead frame 40 are cut off, and the stems 6, 8 bent, giving a completed sensor 2 (FIG. 4 (d))

Second to Fourth Embodiments

Figure 5:
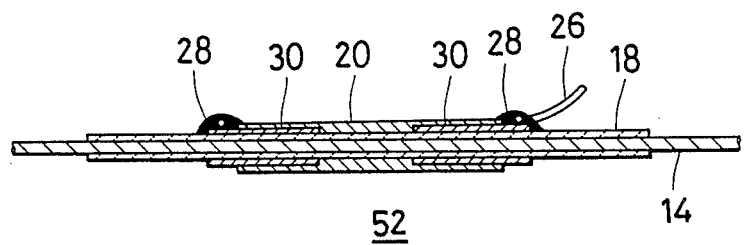
FIG. 5 is a fragmentary view in section of a second embodiment.

FIG. 5 shows a second embodiment, i.e. a sensor 52. To give greater resistance to the heat generating member 14 rather than to achieve a saving in power, the sensor 52 includes no conductor coating 16 of gold. The sensor 52 has gold film electrodes 28 formed on the insulating coating 18 as by vacuum evaporation, and a gold paste electrode 29 joined to each electrode 30 so as to improve the connection between the sensitive layer 20 and the electrode 30.

Figure 6:
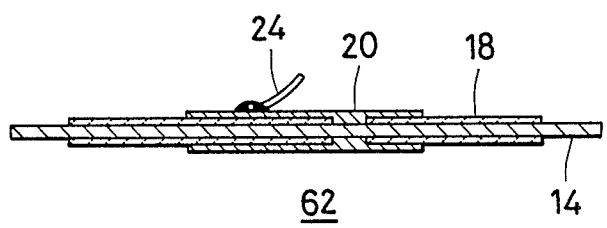
FIG. 6 is a fragmentary view in section of a third embodiment.

FIG. 6 shows a sensor 62 comprising a heat generating member 14 of noble metal. Beneath the sensitive layer 20, the insulating coating 18 is partially removed to hold the layer 20, joined to the electrode 24, in contact with the member 14, which therefore serves as the other electrode.

Figure 7:
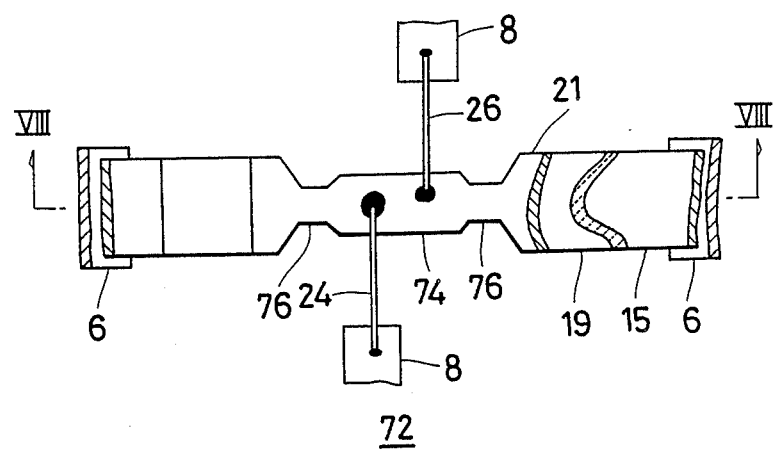
FIG. 7 is a fragmentary front view of a fourth embodiment.
Figure 8:
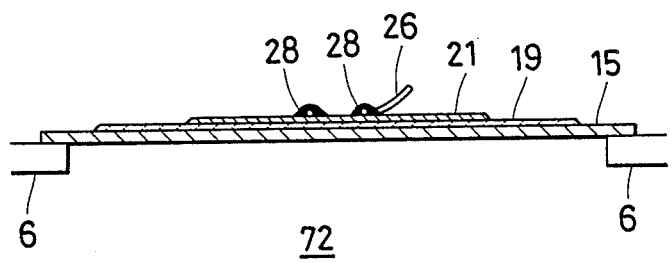
FIG. 8 is a view in section taken along the line VIII—VIII in FIG. 7.

FIGS. 7 and 8 show another sensor 72 comprising a heat generating member 14 in the form of a plate. The member 14 is coated with a heat-resistant insulating coating 19, on which an atmosphere-sensitive layer 21 is provided as by printing. The plate member 15 has a bridge portion 74 and a portion 76 of reduced width at each end of the bridge portion 74 so as to inhibit heat conduction.

Attached Circuit

The problem associated with these sensors is that the heat generating member 14 has a low resistance value. The provision of atmosphere-sensitive layers and the characteristics thereof are known since such layers are used in sensors of the thin or thick film type. The problem resides solely in the resistance value of the heat generating member 14. Gas sensors are used generally at a temperature of about 300° to about 400° C. Humidity sensors, when heat-cleaned, are operated generally at about 300° C. In the case of proton conductors, the operating temperature is generally at room temperature to about 200° C. For use at room temperature, the conductor is heat-cleaned at about 300° C. usually Table 1 shows the heater characteristics achieved by heat generating members 14 in the form of a wire when the distance between the stems 6, 6 was 2 mm.

TABLE 1

| Material and wire diam. (μm) | Heater characteristics* | |
| --- | --- | --- |
| | Resistance (Ω) | Power (mW) |
| Pd-Ir 20 Without Au coating | 3 | 80 |
| Pd 80-Ir 20 With Au coating | 2 | 50 |
| Pt 10 | 3 | 60 |
| Fe—Cr—Al 40 | 3.3 | 100 |

*Resistance: value at room temperature. Power: power required for heating to 300° C. Fe—Cr—Al: Kanthal alloy. Lead wires 24, 26: Au wires, 20 μm in diameter.

Figure 9:
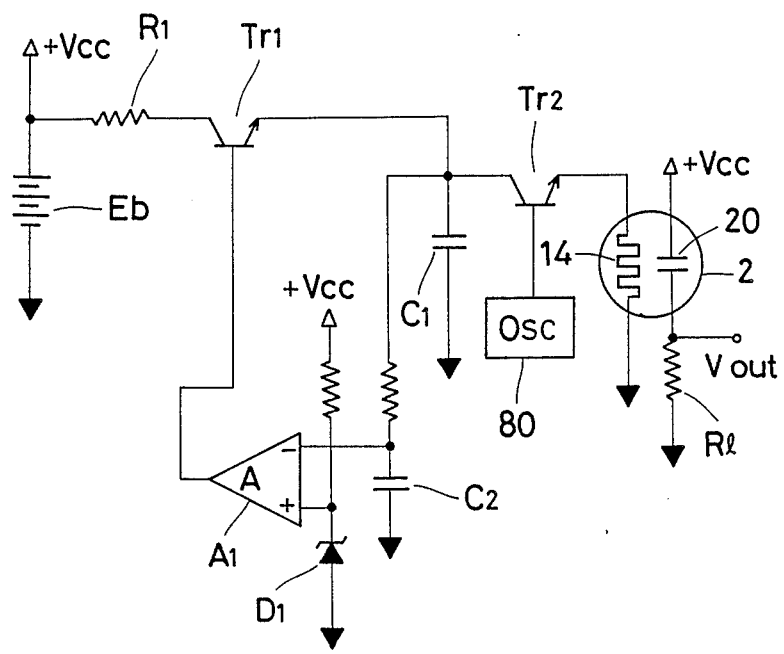
FIG. 9 is a diagram showing a circuit attached to the sensor of the first embodiment.

The conditions for obtaining 80-mW power using a 3-ohm heat generating member 14 are approximately 500 mV and 170 mA. The voltage of 500 mV is low, so that it is difficult to stabilize the power supply. When a power supply of about 5 V which is usually used is dropped to 0.5 V, the voltage drop of the power supply is great, leading to a power loss and necessitating a greater power supply Further the current needed is as great as 100 to 200 mA, necessitating a power supply of increased capacity FIG. 9 shows a circuit as attached to the sensor 2 of FIG. 1 and designed with consideration given to the above situation. Indicated at Eb is a stabilized power supply of about 5 V for giving an output Vcc to the components of the circuit. The circuit comprises a protective resistor R1 of about 10 ohms, transistor Tr1, capacitor C1 of about 100 microfarads, transistor or like switch Tr2, oscillation circuit 80 for producing pulses at a frequency of about 1 KHz at a duty ratio of about 1/100, load resistor of about 100 kiloohms, capacitor C2 for smoothing the output of the capacitor C1, Zener diode D1 for producing a reference potential and error amplifier A1.

Figure 11:
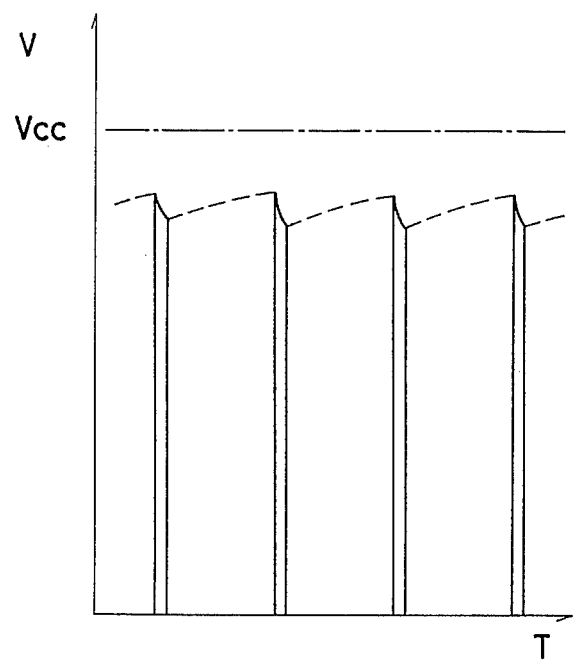
FIG. 11 is a characteristics diagram of the circuits of FIGS. 9 and 10.

FIG. 11 shows the operation characteristics of the circuit. The capacitor C1 is charged with the output of the power supply Eb through the protective resistor R1 and the transistor Tr1. The voltage of the capacitor C1 is delivered via the capacitor C2 and compared with the reference potential to control the transistor Tr1 and render the voltage of capacitor C1 constant. When the transistor Tr2 is in conduction, the heater 14 is energized with pulses to heat the sensor. Since the capacitor C1 is used in this case, the load on the power supply Eb is substantially constant, the load current thereof being about 20 mA. Thus, the load current is small, and the burden on the power supply Eb is small. The sensor 2 is heated with pulses of about 1 KHz, so that the duration of heating is sufficiently smaller than the thermal time constant of the sensor which is about 100 msec. Consequently, the load current through the power supply is small, diminishing the power loss due to a voltage drop. Nevertheless, the sensor is maintained at a constant temperature. Since the capacitance of the capacitor C1 is likely to vary with the lapse of time, the time constant of the capacitor and the member (resistance ) 14 is made sufficiently longer than the duration of each pulse. In the present case, the capacitor is 100 microfarads in capacitance, the resistance is 3 ohms and the time constant is about 300 microseconds. On the other hand, the pulse width is about 10 microseconds, and the output of the capacitor C1 remains constant during the pulse duration irrespective of the capacitance. Desirable conditions for the circuit are that the on-off frequency of the transistor Tr2 is at least 5 times the thermal time constant of the sensor and that the capacitance of the capacitor C1 in terms of the time constant thereof and the heater 14 is at least 5 times the pulse width.

The pulse width of the transistor Tr2 is automatically determined from the on-off frequency and the duty ratio required for heating. The transistor Tr2 may be connected directly to the power supply Eb without stabilizing the voltage by the error amplifier A1, etc, and smoothing the power supply load by the capacitor C1.

Next, a load resistor R1 is connected to the sensitive layer 20 to accomplish detection from the output Vout. In the case of a humidity sensor, the heater is not used usually, but the heater is energized for heat cleaning. With sensors wherein the electromotive force of a proton conductor or the like is utilized, the electromotive force of the sensitive layer 20 is measured.

Figure 10:
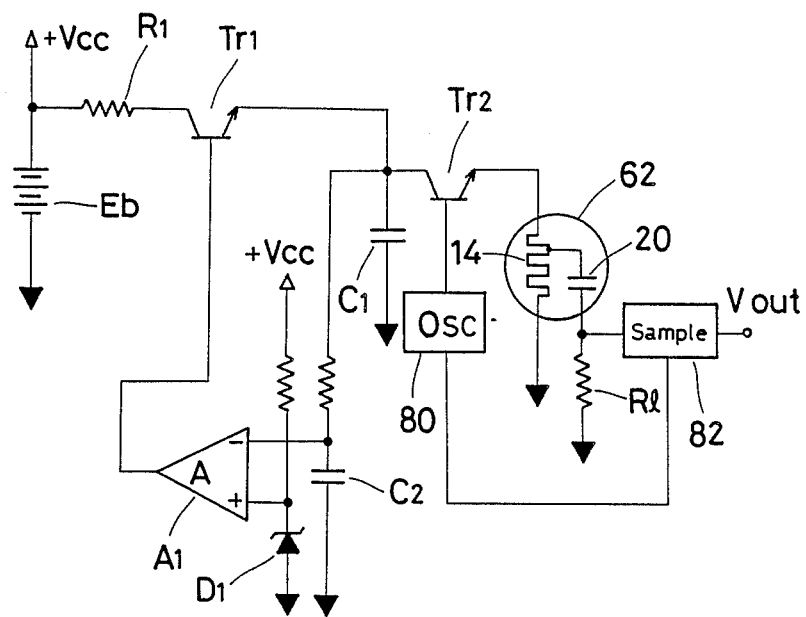
FIG. 10 is a diagram showing another attached circuit.

FIG. 10 shows a circuit for the sensor 62 wherein the heat generating member 14 serves also as an electrode. With this sensor, the voltage to be applied to the sensitive layer 20 is derived from the heater voltage. In this circuit, a sampling circuit 82 is operated with pulses timed with the conduction of a transistor Tr2 to remove noises due to on-off action of the power supply. Such a sampling circuit is already known. The circuit can be an integration circuit merely comprising a capacitor and resistor Sensor Characteristics The characteristics of a gas sensor wherein $SnO_2$ is used for illustrative purposes An F-Cr-Al alloy wire 14, 40 micrometers in diameter, was coated with alumina as at 18 to a thickness of about 1 micrometer by plasma CVD. An $SnO_2$ film (97 wt. % $SnO_2$ and 3 wt. % of PdO as a catalyst) was formed on the coating 18 by sputtering to obtain an atmosphere-sensitive layer 20 having a thickness of about 5000 angstroms. Lead wires 24, 26, 20 micrometers in diameter, were attached to the layer 20 with gold paste electrodes 28 to complete a sensor.

The heat generating member 14 obtained was 3.3 ohms in resistance value at room temperature, required power of 100 mW for heating to 300° C. and had a thermal time constant of about 100 msec. When the member 14, lead wire 24, etc. are made diametrically smaller, improvements can be apparently achieved in power consumption, heat capacity, thermal time constant and heater resistance. The insulation resistance between the electrode and the member 14 was about 10 megaohms When subjected to 100 room temperature-800° C. heat cycles by energizing the member 14, the member 14 remained unchanged in the insulation resistance.

In the absence of the insulating coating 18, the Fe-Cr-Al alloy wire of the sensor is gradually corroded when exposed to about 1000 ppm of $SO_2$ or $H_2S$. However, the alumina coating formed shielded the alloy wire 14 from the atmosphere, precluding the corrosion of the wire. Further since the $SnO_2$ layer is low in its strength to bond to metal surfaces, the layer, if directly formed on the wire 14, becomes separated due to the stress acting between the lead wires 24, 26 and the $SnO_2$ layer. However, the alumina coating affords improved bond strength to prevent the layer from separation. The alumina layer may have incorporated therein various additives when required and may be further coated with a suitable oxidizing catalyst to remove objectionable gases on oxidation.

Figure 12:
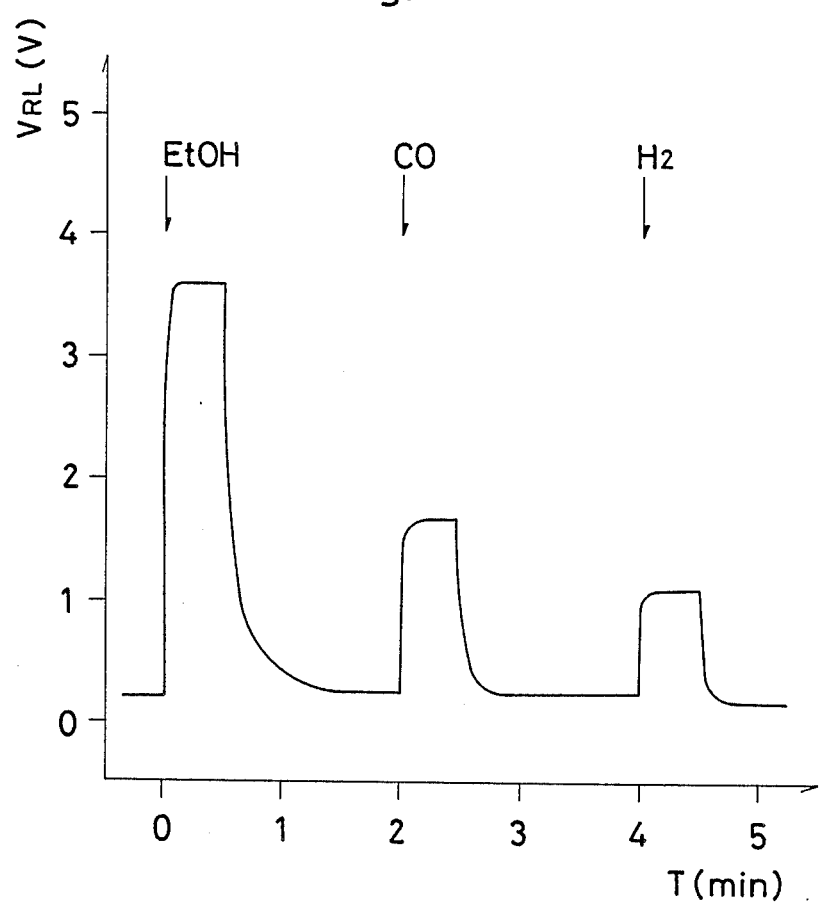
FIG. 12 is a diagram showing the gas detection characteristics of an embodiment.

Using atmospheres having a temperature of 20° C. and a relative humidity of 65%, the sensor was checked for resistance in air and in 1000 ppm of each of ethanol, CO, $H_2$ and isobutane. Isobutane is typical of combustible gases. FIG. 12 shows the response characteristics to ethanol, CO and $H_2$ at 300° C. Table 2 shows the resistance measurements obtained at 300° C., and Table 3 those at 400° C.

TABLE 2

| Sensor characteristics 300° C. | |
| --- | --- |
| Atmosphere | Resistance value ($\Omega$) |
| Air | 2.4 M |
| Ethanol | 40 K |
| CO | 200 K |
| $H_2$ | 350 K |

TABLE 3

| Sensor characteristics 400° C. | |
| --- | --- |
| Atmosphere | Resistance value ($\Omega$) |
| Air | 1.2 M |
| Ethanol | 50 K |
| Isobutane | 400 K |
| $H_2$ | 300 K |

Fifth Embodiment

The embodiments of FIGS. 1 to 8 have the problem that the metal heat generating members 14 and 15 are too small to handle easily. This problem can be overcome by preparing an assembly of many lead frames each having a heat generating member attached thereto for connection to external leads. FIGS. 13 to 19 show such an embodiment. The parts similar to those of the embodiment of FIGS. 1 to 4 are each designated by a similar corresponding reference numeral. What has been disclosed about the embodiments of FIGS. 1 to 8, the circuits of FIGS. 9 and 10 and the characteristics shown in FIGS. 11 and 12 are true of or useful for the present invention similarly.

The sensor of the present embodiment is fabricated by the following process. An external lead frame 132 is prepared from 42 alloy (56 wt. % iron, 42 wt. % nickel, Co, Mn, Si, etc.), nickel or the like (FIG. 13). The lead frame 132 comprises four external leads 134 which are joined together. Indicated at 136 is an external lead identifying mark, and at 138 a hole for positioning the lead frame. A base 140 is molded integrally with the lead frame 132 and is joined to an unillustrated uppper cover later to provide a sensor housing. The base 140 has a space for accommodating a metal heat generating member. Preferably, an assembly of lead frames 132 is used, the number of frames being equal to the number of sensors to be attached to the assembly. However, the sensor may be assembled for each base 140 without using any external lead frame 132. The base 140 may be attached after the heating member has been connected to the parts concerned.

Aside frame the above procedure, a lead frame for the metal heat generating member is prepared (FIG. 14). A portion of the lead frame 142 is used for the generating member 114. Branches 144, 146 are joined to the member 114 into the lead frame 142. Indicated at 148 are holes for use in positioning the frame 142 relative to the external lead frame 132. Preferably lead frames 142 are provided as a unit for about 10 sensors.

Figure 15A:
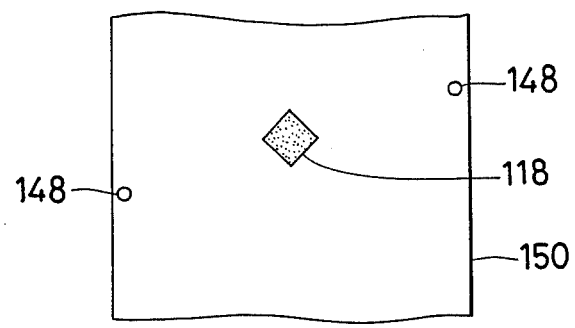
FIGS. 15 (a) to (c) are plan views showing a process for preparing the lead frame of FIG. 14.
Figure 15B:
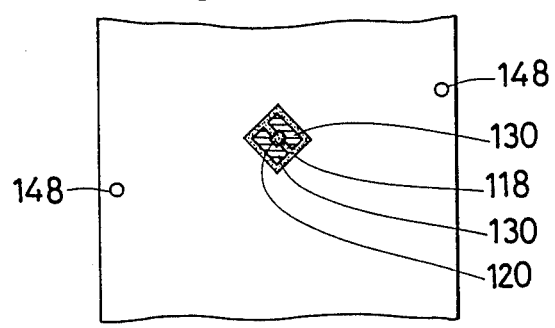
Figure 15C:
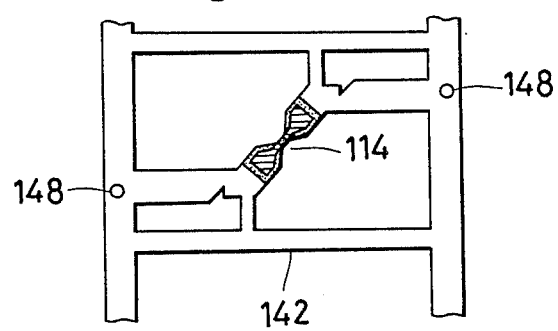

The lead frame 142 is produced by the following method (FIGS. 15 (a) to (c)). A thin plate 150 of the material for the metal heat generating member is prepared, and the positioning marks 148 are formed therein. The material to be used for the member 114 is, for example, a noble metal such as Pt, Ir, Pt-ZGS (wherein $ZrO_2$ particles are separated out at the grain boundary of Pt) or Pd-Ir alloy (80 wt. % Pd and 20 wt. % Ir), or a base metal such as Fe-Cr-Al alloy, Ni-Cr alloy or W.

After suitably masking the surface of the thin plate 150, a heat-resistant insulating coating 118 is formed on the plate (FIG. 15 (a)). The coating 118 may be the same as those of the embodiments of FIGS. 1 to 8 in respect of material, method of forming, thickness, etc.

A pair of gold, platinum or like electrodes 130, 130 are formed on the coating 118 as by printing or vacuum evaporation. Further formed on the electrodes 130 is a thin or thick layer 120 of a metal oxide semiconductor whose resistance value varies when it is exposed to a gas or water vapor, such as $SnO_2$ or $In_2O_3$, whereby an atmosphere-sensitive layer is formed (FIG. 15 (b)). The layer 120 can be formed by sputtering, thin film forming techniques such as the thermal decompostion of the starting material for sputtering, or thick film forming techniques such as powder printing. The order in which the electrodes 130 and the layer 120 are formed is suitably variable.

Although the above-mentioned semiconductor is used as an example of gas sensitive material in the above description, also usable are a material, such as $MgCr_2O_4$ or $TiO_2$ which exhibits an altered resistance value on adsorption of water vapor, a proton conductor, such as antimonic acid ($H_2Sb_2O_6$) or antimony phosphate ($HSbP_2O_8$), which produces an electromotive force when exposed to hydrogen, or a solid electrolyte, such as $ZrO_2$, which produces an electromotive force on contact with oxygen.

After the sensitive layer 120 and electrodes 130 have been formed, a specified pattern of resist is printed on the plate 150. The lead frame 142 is completed, for example, by subsequently subjecting the rear side of the plate 150 to etching (FIG. 15 (c)).

Figure 16:
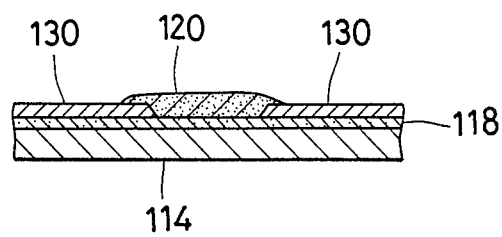
FIG. 16 is an enlarged fragmentary view in section showing the metal heat generating member of the fifth embodiment.
Figure 17:
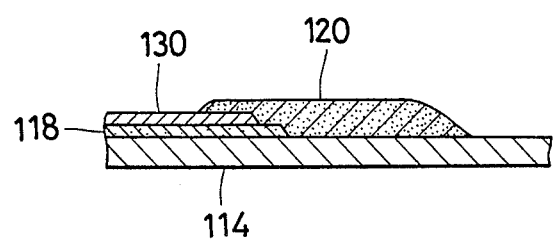
FIG. 17 is an enlarged fragmentary view in section showing a modification of the heat generating member of the fifth embodiment.

FIG. 16 is a fragmentary view showing the product obtained by the process of FIG. 15. The member 114, when made of noble metal, may serve also as one of the electrodes on the sensitive layer 120. FIG. 17 shows such an example.

Figure 18:
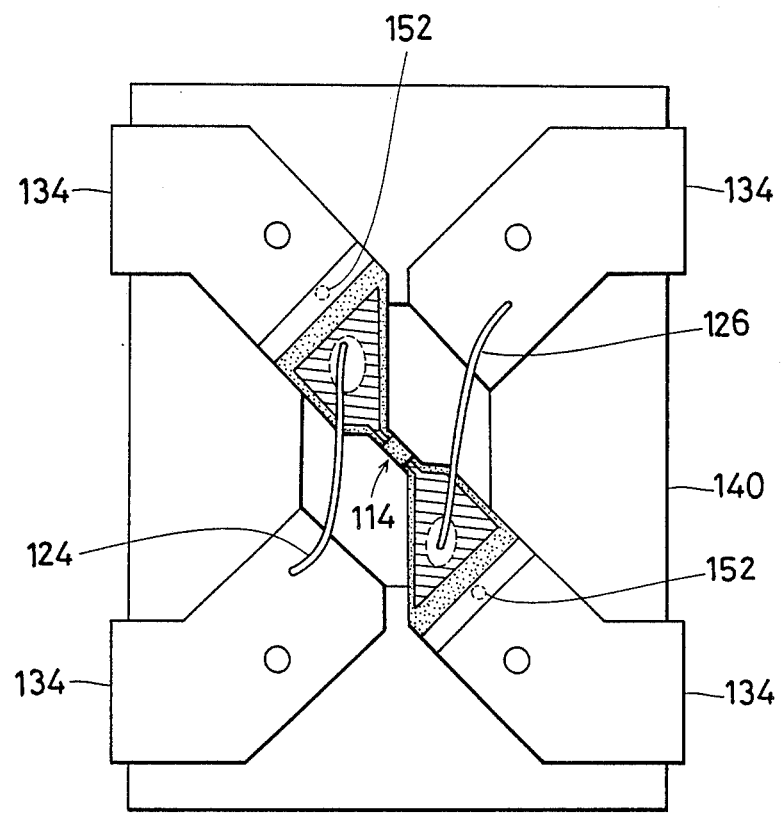
FIG. 18 is a plan view of the gas sensor of the fifth embodiment.
Figure 19:
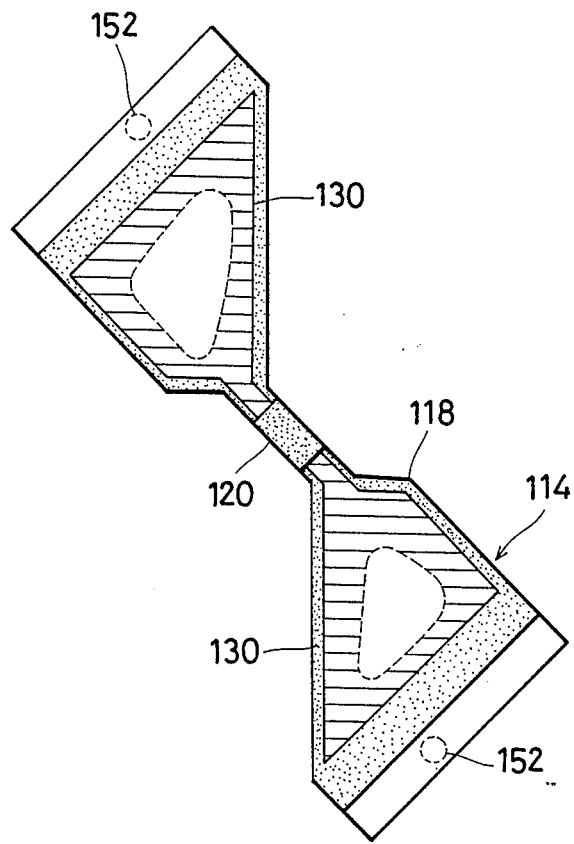
FIG. 19 is an enlarged fragmentary plan view of FIG. 18.

FIG. 18 is a front view showing the completed sensor, and FIG. 19 is a fragmentary view showing the same. The lead frame 142 is positioned properly on the external lead frame 132, and the member 114 is welded to two of the external leads 134 as at 152. The two lead frames can be easily fitted together in position with reference to the marks 138, 148 or with use of a pattern recognition device for use in the fabrication of ICs or the like. Next, the electrodes 130, 130 are connected to the remaining two external leads 134 with gold or like lead wires 124, 126 by wire bonding. The unnecessary portions are thereafter cut off from the lead frames 132, 142, the external leads 134 are bent, and an unillustrated upper cover is secured to the base 140, whereby a completed sensor can be obtained. Preferably, the inner ends of the leads 134 concerned are arranged under the portions of the lead wires 124, 126 to be welded for supporting the load involved in welding. At the opposite sides of the sensitive layer 120, the heat generating member 114 is made to have an increased width to assure the external leads 134 and the lead wires 124, 126 of ease of welding and to inhibit useless evolution of heat at the portions thereof except where the layer 120 is present.

The sensor of the present embodiment is equivalent to those of FIGS. 1 to 8 in detection characteristics. Next, a sensor having the following specifications according to the present embodiment was checked for power consumption as an example. An Fe-Cr-Al alloy plate having a thickness of 20 micrometers was used as the heat generating member 114. The member 114 was 300 micrometers in the length of its bridge portion bearing the sensitive layer 120 and 50 micrometers in width. The sensitive layer 120 was a printed $SnO_2$ layer with a thickness of 10 micrometers. The insulating coating 118 was a one-micrometer-thick alumina coating, and the electrodes 130, 130 were gold electrodes with a thickness of 0.5 micrometer. The member 114 was about 0.5 ohms in resistance value and required power of about 30 mW for heating from room temperature to 400° C. If the member 114 is made smaller, the power consumption further diminishes.

According to the present embodiment, the sensitive layer 120, the insulating coating 118 and the electrodes 130 are easy to form and can be positioned with high precision. The member 114 and the lead wires 124, 126 can also be attached to the external leads 134 easily.

Six Embodiment

Figure 20:
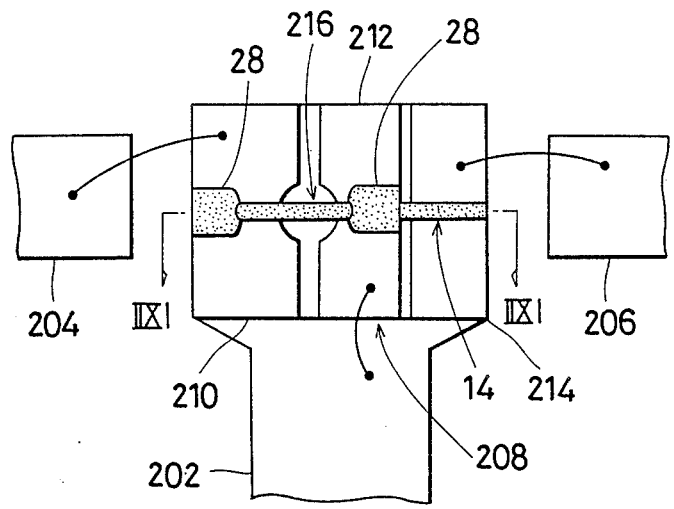
FIG. 20 is a fragmentary plan view of a sixth embodiment.
Figure 21:
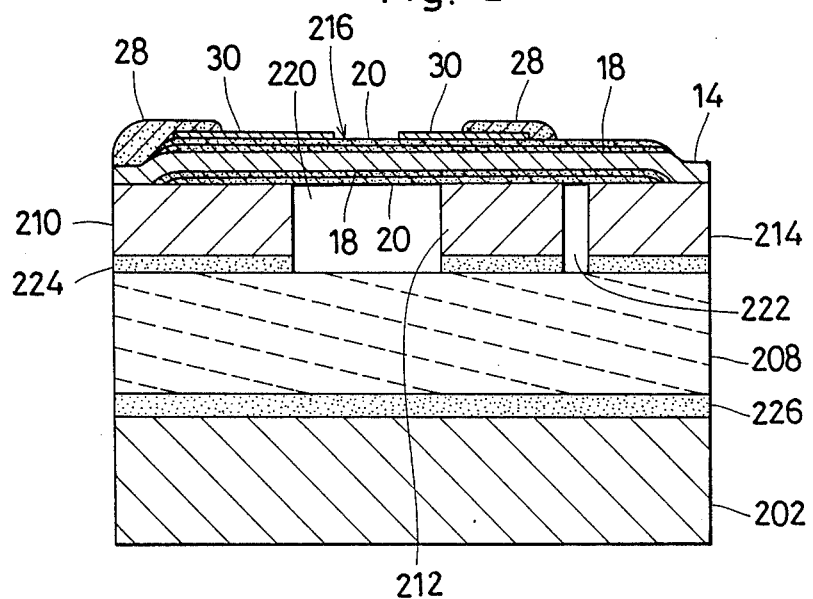
FIG. 21 is an enlarged fragmentary view in section taken along the line XXI—XXI in FIG. 20.

With the embodiment of FIGS. 1 to 4, the lead wires 24 and 26 are connected to the heat generating member 14, whereas it is difficult to attach the wires 24, 26 to the small member 14. The purpose of using the lead wires 24, 26 is to reduce the heat loss involved. However, when the member 14 itself is small-sized, the electrodes joined to the sensitive layer 20 can be connected directly to external electrodes without using lead wires. FIGS. 20 and 21 show such an embodiment. Throughout FIGS. 1 to 8 and FIGS. 20 and 21, like parts are designated by like reference numerals. Such parts are the same as those already described in the method of formation, characteristics, etc.

With reference to FIG. 20, external leads 202, 204, 206 are secured to an unillustrated housing. An alumina or like insulating substrate 208 is adhered to the upper surface of the external lead 202 by die bonding. The alumina substrate 208 is provided with three external electrodes 210, 212, 214, to which a sensor main body 216 is bonded. The sensor main body 216 compirses a metal heat generating member 14 in the form of a wire and entirely covered with a heat-resistant insulating coating 18 of alumina or the like and with an atmosphere-sensitive layer 20 of $SnO_2$ or the like. A pair of film electrodes 30, 30 is joined to the layer 20. One of the electrodes 30 is connected to the external electrode 210, and the other electrode 30 to the external electrode 212 with gold paste portions 28, 28.

With reference to FIG. 21, a process for fabricating this sensor will be described. An insulating coating 18 and an atmosphere-sensitive layer 20 of $SnO_2$ are formed over the entire surface of a metal heat generating member 14. Aside from this step, a die is prepared which has bonded thereto external electrodes 210, 212, 214. The member 14 is welded at its opposite ends to the die. The member 14 is weldable without removing the coating 18 and $SnO_2$ layer 20. The die has slits 220, 222 for separating the external electrodes 210, 212, 214 from one another. Film electrodes 30, 30 are thereafter provided on the layer 20. Using a gold paste 28, the electrodes 30, 30 are connected to the external electrodes 210, 212, respectively.

Subsequently, the die is bonded to an alumina substrate 208 with an adhesive. The die and the alumina substrate 208 are then cut to obtain one sensor in the form of a chip. The alumina substrate 208 is used to prevent the sensor main body 216 from breaking when the die is cut. The chip can be prepared similarly also when the external electrodes 210, 212, 214 are printed on the alumina substrate 208 as film electrodes before the welding of the metal member 14.

The separated chip is bonded to an external lead 202 with an adhesive 226, and the external electrodes 210, 212, 214 are connected to the external leads 202, 204, 206 by wire bonding, whereby the sensor of FIG. 20 can be obtained.

According to the present embodiment, a sample was prepared in the following manner and checked for characteristics.

A wire 14 of Fe-Cr-Al alloy (Kanthal alloy) having a diameter of 20 micrometers was coated with alumina sol, which was then subjected to thermal decomposition at 800° C. This step was repeated 10 times to form an alumina coating 18, about 1 micrometer in thickness, over the entire surface of the wire 14 serving as a heat generating member. An isobutanol solution of an organic compound of Sn, i.e. $Sn(OCH_3)_3 \cdot (O(CH_2)_3NH_2)$, was sprayed on the coating 18, followed by thermal decomposition at 500° C. to form $SnO_2$.

Subsequently, the wire 14 was cut to a length of 1 mm, and the cut wire was directly welded to external electrodes 210, 214. The wire was weldable without removing the insulating coating 18 and $SnO_2$ layer 20 since they were removed by the welding pressure and welding current.

With the welded wire 14 masked, gold electrodes 30, 30 were formed on the layer 20 by vacuum evaporation. The electrodes 30, 30 were thereafter connected to the external electrodes 210, 212 with a gold paste 28. Table 4 shows the characteristics of the sensor thus obtained when the temperature of the SnO₂ layer 20 was 270° C.

TABLE 4

| | |
|---|---|
| Length of wire 14 | 1 mm |
| Power consumption | 40 mW (0.4 V × 4Ω) |
| Insulation resistance | at least 5 MΩ |
| Resistance value in air | 500 KΩ (20° C., R.H. 65%) |
| Gas sensitivity | |
| Methyl mercaptan 1 ppm | about 60 |
| Ethyl alcohol 100 ppm | about 10 |

*The insulation resistance was measured between the SnO₂ layer 20 and the external electrode 214. The gas sensitivity is expressed in the ratio of resistance value of the SnO₂ layer 20 in air to that in the gas.

What is claimed is:

1. A gas sensor consisting essentially of:
   at least three planar metal outer electrodes;
   a wire metal heat generating member connected to and supported by two of the three planar metal outer electrodes;
   a heat resistant insulating coating formed on the wire metal heat generating member;
   a gas-sensitive layer formed on the heat resistant insulating coating, electrical characteristics of the gas-sensitive layer changing with changes in an environmental gas to be sensed; and
   at least one detecting electrode formed at a position selected from the group consisting essentially of the heat resistant insulating coating and the gas-sensitive layer, and said at least one detecting electrode connected to the gas-sensitive layer and directly connected to the remaining planar metal outer electrode.

2. A gas sensor defined in claim 1, wherein the at least one detecting electrode comprises a conducting film which is in contact with the gas-sensitive layer, and a conductive paste which is in contact with the conductive film and the remaining planar metal outer electrode to directly connect both the conducting film and the remaining planar metal outer electrode.

3. A gas sensor defined in claim 1, wherein the heat generating member is made of Ni-Cr alloy or Fe-Cr-Al alloy.

4. A gas sensor defined in claim 1, wherein the heat generating member is welded, at each end, to the two of the three planar metal outer electrodes.

5. A gas sensor defined in claim 1, further including a heat resistant insulating substrate, wherein the three planar metal outer electrodes are connected to the heat resistant insulating substrate and supported by the heat resistant insulating substrate on a side of the heat resistant insulating substrate which is opposite the heat generating member.

6. A gas sensor defined in claim 5, further including a housing and at least three external leads attached to the housing, and the three planar metal outer electrodes are connected to the external leads by wire bonding.

* * * * *